(12) United States Patent
Perry

(10) Patent No.: US 10,172,801 B1
(45) Date of Patent: Jan. 8, 2019

(54) BIOMEDICALLY ACTIVE AND DELIVERY SITE SPECIFIC CAPSULE-IN-CAPSULE LIVER SUPPLEMENT APPARATUS AND METHOD OF USE THEREOF

(71) Applicant: Bruce Perry, Carefree, AZ (US)

(72) Inventor: Bruce Perry, Carefree, AZ (US)

( * ) Notice: Subject to any disclaimer, the term of this patent is extended or adjusted under 35 U.S.C. 154(b) by 0 days.

(21) Appl. No.: 15/645,954

(22) Filed: Jul. 10, 2017

(51) Int. Cl.
| | | |
|---|---|---|
| *A61K 9/48* | (2006.01) | |
| *A61K 31/14* | (2006.01) | |
| *A61K 31/7076* | (2006.01) | |
| *A61K 31/56* | (2006.01) | |
| *A61K 31/36* | (2006.01) | |
| *A61K 45/06* | (2006.01) | |
| *A61K 36/28* | (2006.01) | |
| *A61K 36/738* | (2006.01) | |
| *A61K 36/78* | (2006.01) | |
| *A61K 36/744* | (2006.01) | |
| *A61K 36/69* | (2006.01) | |
| *A61K 36/815* | (2006.01) | |

(52) U.S. Cl.
CPC .......... *A61K 9/4808* (2013.01); *A61K 9/4858* (2013.01); *A61K 9/4891* (2013.01); *A61K 31/14* (2013.01); *A61K 31/36* (2013.01); *A61K 31/56* (2013.01); *A61K 31/7076* (2013.01); *A61K 36/28* (2013.01); *A61K 36/69* (2013.01); *A61K 36/738* (2013.01); *A61K 36/744* (2013.01); *A61K 36/78* (2013.01); *A61K 36/815* (2013.01); *A61K 45/06* (2013.01); *A61K 2236/33* (2013.01)

(58) Field of Classification Search
None
See application file for complete search history.

(56) References Cited

U.S. PATENT DOCUMENTS

2005/0123628 A1\* 6/2005 Zabrecky ............. A61K 31/352
424/725

\* cited by examiner

*Primary Examiner* — Robert A Wax
*Assistant Examiner* — Melissa S Mercier
(74) *Attorney, Agent, or Firm* — Kevin Hazen

(57) ABSTRACT

The invention comprises a biomedically active/delivery site specific capsule-in-capsule liver supplement and method of use thereof. A first set of constituents, of an outer capsule, of a capsule-in-capsule liver supplement, comprises one or more of choline and phosphatidylcholine; a second set of constituents, of an inner capsule, comprise one or more of methionine, glycyrrhetinic acid, silymarin, and phosphatidylcholine; and either capsule optionally contains one or more liver aiding/regulating natural products, where the outer capsule dissolves in the stomach and the inner capsule dissolves in the small intestine. Thus, the dual dissolution process in controlled environments results in complementary and synergistic delivery of liver regulating molecules in a bioavailable form ready for transport through the wall of the small intestine. Further, constituents of the capsule-in-capsule liver supplement include multiple inputs into the methionine cycle, which facilitates/synergistically aids the body's use of the methionine cycle, such as in liver regulation.

16 Claims, 3 Drawing Sheets

BIOMEDICALLY ACTIVE AND DELIVERY SITE SPECIFIC CAPSULE-IN-CAPSULE LIVER SUPPLEMENT APPARATUS AND METHOD OF USE THEREOF

BACKGROUND OF THE INVENTION

Field of the Invention

The invention relates to a biomedically active and site specific, capsule-in-capsule liver supplement delivery system.

Discussion of the Prior Art

The human body utilizes interlinked biochemical pathways to maintain system health. Hence, a restriction in one metabolic pathway often affects multiple linked pathways. Similarly, facilitating a pathway often benefits related/linked body systems. One critical pathway is the methionine cycle. In the methionine cycle, S-adenosyl methionine circulates in the blood and functions as a methyl donor. Donating a methyl group to other molecules can accelerate or preserve reactions in the body as a form of metabolic maintenance. Thus, the body benefits from an adequate supply of S-adenosyl methionine in the bloodstream.

A lack of adequate intake of methionine is associated with development of fatty liver disease. What is needed is a system for delivering bioactive methionine to the body.

SUMMARY OF THE INVENTION

A biomedically active and site specific, capsule-in-capsule liver supplement delivery system is described.

BRIEF DESCRIPTION OF THE DRAWINGS

A more complete understanding of the present invention is derived by referring to the detailed description and described embodiments when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF EXEMPLARY EMBODIMENTS

The invention comprises a biomedically active/delivery site specific capsule-in-capsule liver supplement and method of use thereof. Generally, a first set of constituents, of an outer capsule, of the capsule-in-capsule liver supplement comprises one or more of choline and phosphatidylcholine; a second set of constituents, of an inner capsule, comprise one or more of methionine, glycyrrhetinic acid, Silymarin, and phosphatidylcholine; and either capsule optionally contains one or more liver aiding/regulating natural products. Thus, the constituents of the capsule-in-capsule liver supplement include multiple inputs into the methionine cycle, which facilitates/synergistically aids the body's use of the methionine cycle, such as in liver regulation.

Liver Protocol/Enhancement

Figure 1:
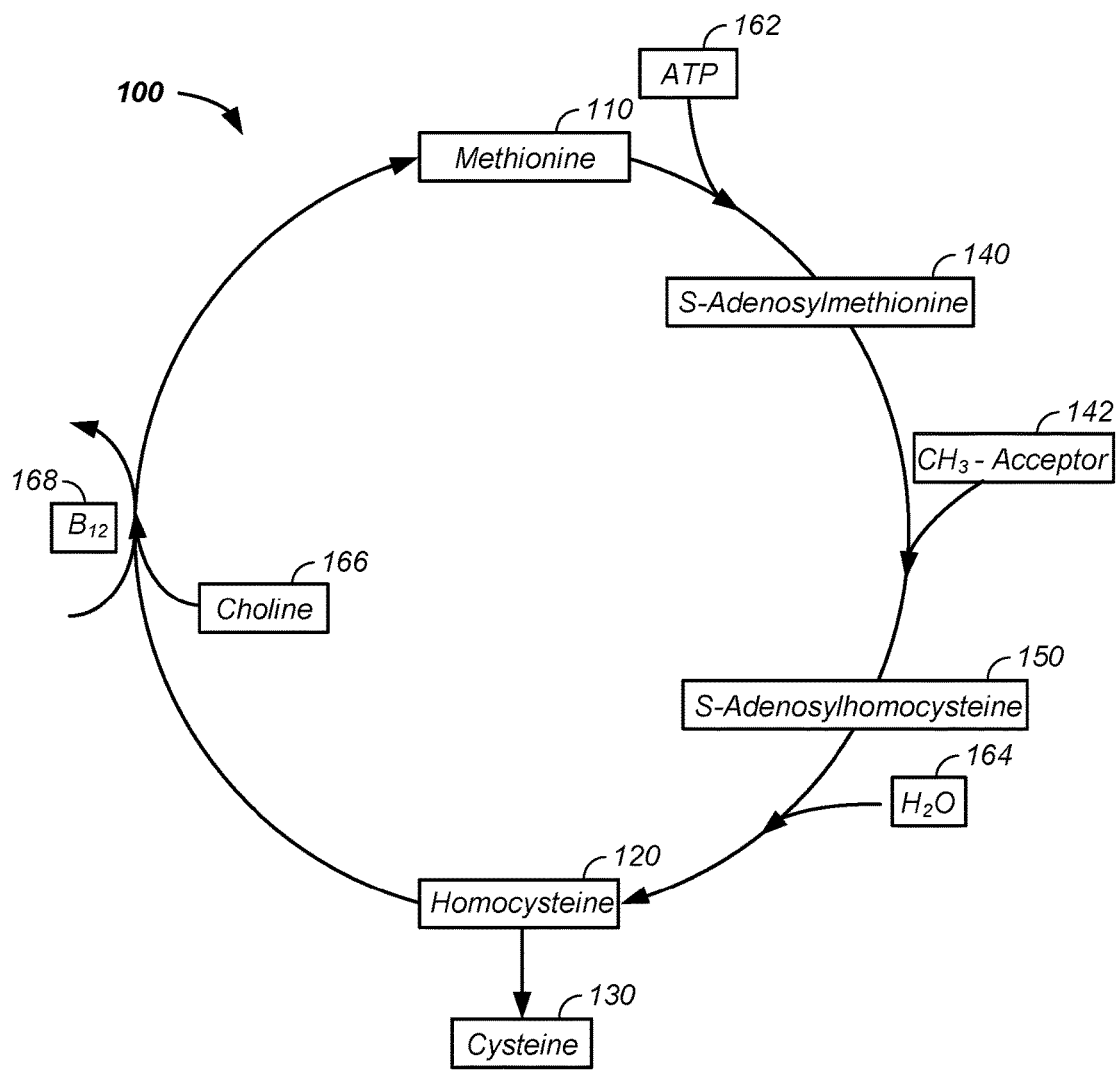
FIG. 1 illustrates the methionine cycle.

Referring now to FIG. 1, a simplified version of the methionine cycle 100 is illustrated. In the methionine cycle 100, methionine 110 is converted to homocysteine 120 and eventually cysteine 130, by way of S-adenosyl methionine 140 (SAMe) and S-adenosyl homocysteine 150 (SAH). Other relevant components of the methionine cycle 100 include adenosine triphosphate 162 (ATP), water 164, choline 166, and vitamin $B_{12}$ 168. More particularly, ATP 162 is added to methionine 110 to form S-adenosyl methionine 140, which provides a methyl group to a methyl acceptor 142 to form S-adenosyl homocysteine 150 and through addition of water forms homocysteine 120. Homocysteine 120 is either converted back to methionine 110 through the methylation of choline 166, or homocysteine 120 enters the transsulfuration pathway to form other sulfur-containing amino acids. It has been estimated that 60% of homocysteine 120 is metabolized by transsulfuration in the liver.

Some people with liver disease, alcoholic liver cirrhosis, and/or liver failure cannot synthesize S-adenosyl methionine or have a diminished ability to synthesize S-adenosyl methionine. As studies in mice show that S-adenosyl methionine protects against and reverses liver damage, S-adenosyl methionine may help normalize levels of liver enzymes in people with liver disease.

Methyl Donation

Methionine 110 is an essential amino acid containing sulfur. As methionine 110 is an essential amino acid, which cannot be synthesized internally by humans, it must be ingested, typically through dietary proteins. Methionine 110 is essential for the synthesis of proteins and many other biomolecules. A lack of adequate intake of methionine 110 is associated with development of fatty liver disease, which is countered and/or mediated by methionine supplements.

S-Adenosyl Methionine

Figure 2:
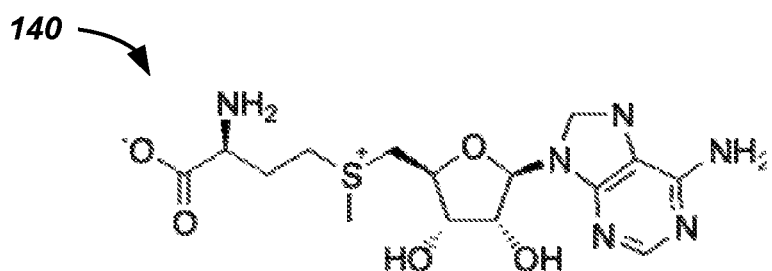
FIG. 2 illustrates SAMe, less the bound adenosine triphosphate.

S-adenosyl methionine 140 is the amino acid methionine 100 bound to a molecule of ATP 162. Referring now to FIG. 2, a non-ATP bound structure of S-adenosyl methionine 140 is illustrated. Referring again to FIG. 1, S-adenosyl methionine 140 circulates in the blood naturally and acts as a methyl donor to the methyl acceptor 142. Donating a methyl group to other molecules can accelerate or preserve reactions in the body as a form of metabolic maintenance. Thus, the body benefits from an adequate supply of S-adenosyl methionine 140 in the bloodstream.

As further described infra, the inventor provides a capsule-in-capsule, also referred to as a dual capsule, liver supplement that releases supplemental methionine 110 and/or methionine 110 in a bioavailable form, such as S-adenosyl methionine 140, in the small intestine after being protected from stomach acids. Further, the capsule-in-capsule liver supplement includes constituents facilitating uptake and use of methionine 110 and/or S-adenosyl methionine 140, again as further described infra. Generally, the capsule-in-capsule liver supplement delivers nutrients to the body in a bioactive form in a region of the body that can absorb the bioactive form, which provides the body the necessary elements of the methionine cycle for self-regulation.

Figure 3:
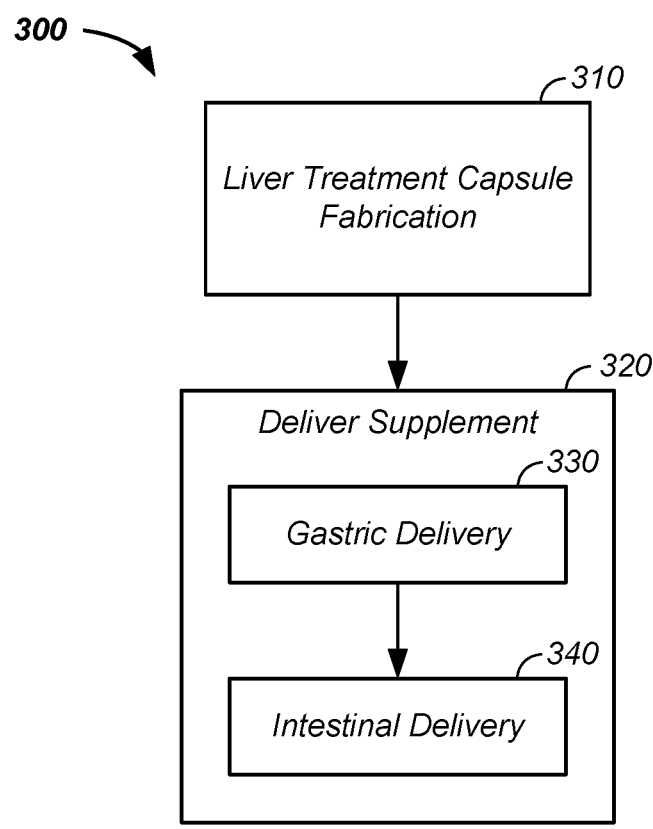
FIG. 3 illustrates a method of generation and use of a capsule-in-capsule delivery system.

Referring now to FIG. 3, a capsule-in-capsule liver supplement method of generation and use 300 is described. Liver treatment capsule-in-capsule fabrication 310 involves placing an inner capsule into an outer capsule, where constituents of the inner capsule and the outer capsule are further described infra. The inventor has determined that use of a phosphatidyl choline suspension of constituents in either capsule to yield a liposome delivery system is enhanced with the addition of de-ionized water, an oil, and/or a fluidization step using a change of temperature. Delivery of the supplement 320 is through ingestion of the dual capsule. Breakdown of the outer capsule is dominantly in a first gastric breakdown delivery stage 330 using acids, enzymes, and/or motions of the stomach and a subsequent breakdown of the inner capsule is dominantly in a second intestinal breakdown delivery stage 340 with uptake through walls of the intestine. Initial breakdown of the outer capsule optionally occurs in the oral cavity. Similarly, initial breakdown of the inner capsule optionally occurs in the stomach.

Capsule-in-Capsule/Dual Capsule

Figure 4:
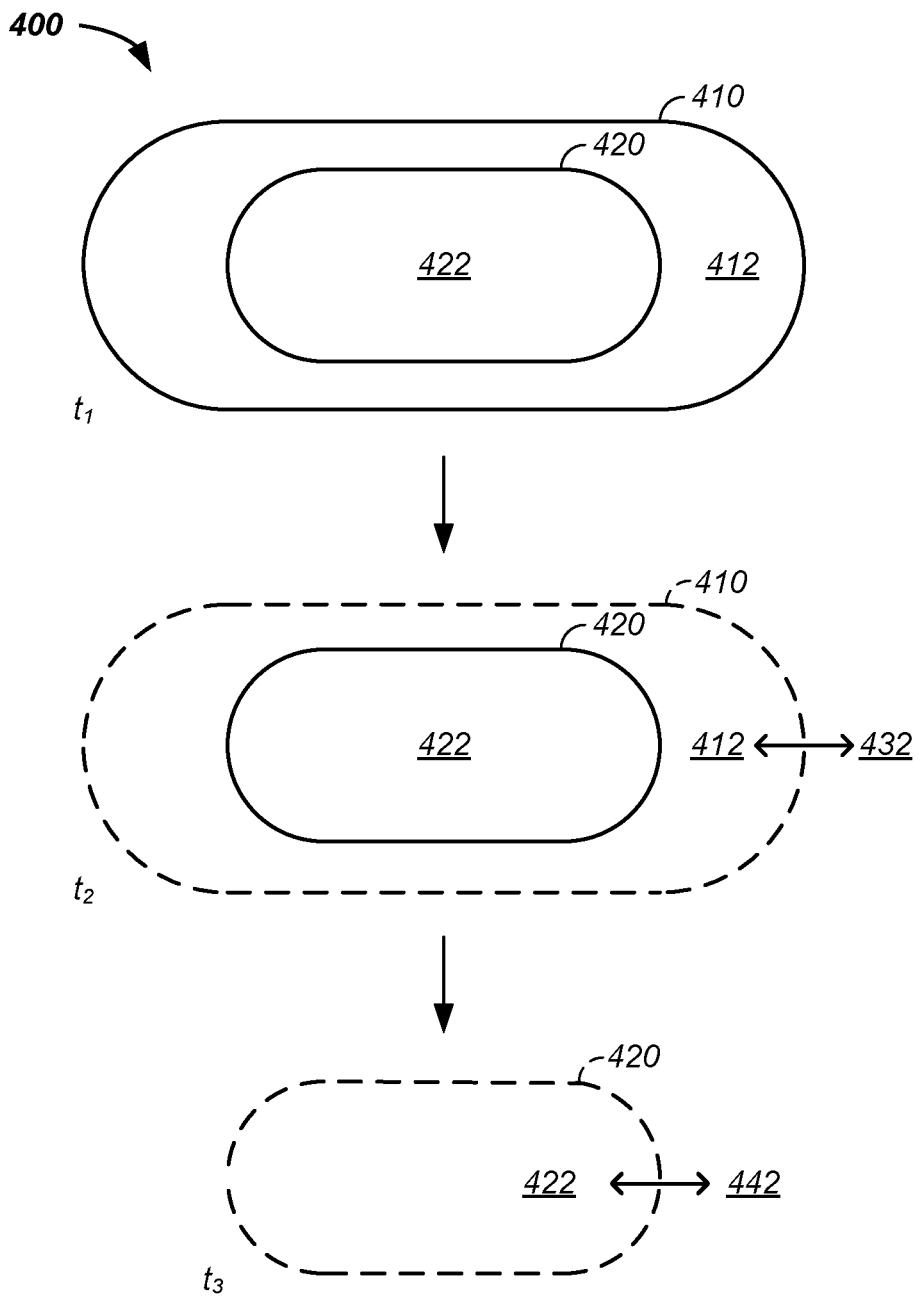
FIG. 4 illustrates a capsule-in-capsule liver supplement.

Referring now to FIG. 4, the capsule-in-capsule delivery system 320 is further described. Generally, a capsule-in-capsule or dual capsule, such as a capsule-in-capsule liver supplement 400, comprises a first capsule or outer capsule 410 that fully encases and/or circumferentially surrounds a second capsule or an inner capsule 420. Herein, a capsule-in-capsule liver supplement 400 is described, where constituents of the outer capsule 420 and the inner capsule 410 are activated, primed, and/or are bioavailable at specific release sites, such as a first digestive track site 432 and a second digestive track site 442, respectively, of a human. For example, the outer capsule 410 is designed to breakdown in the stomach and the inner capsule 420 is designed to fully break down in the intestine. The capsule-in-capsule delivery system 320 facilitates: (1) delivery of a first set of constituents 412, contained in the outer capsule 410, in an acidic environment, such as a human stomach, and (2) delivery of a second set of constituents 422, contained in the inner capsule 420, in the small intestine after passing through the acidic environment of the stomach. The synergistic release of constituents of the dual capsule and/or the release of constituents in respective cavities of the digestive track is further described, infra.

Still referring to FIG. 4, the constituents of the capsule-in-capsule liver supplement 400 are further described. Generally, the first set of constituents 412, of the outer capsule 410, of the capsule-in-capsule liver supplement 400 comprises one or more of choline 166 and phosphatidylcholine. Generally, the second set of constituents 422, of the inner capsule 420, comprise one or more of: methionine 110, glycyrrhetinic acid, Silymarin, and phosphatidylcholine. Either capsule of the capsule-in-capsule liver supplement 400 optionally contain any vitamin and/or natural product identified as beneficial to liver regulation and/or for liver treatment, such as vitamin $B_{12}$ 168; folate, such as folic acid and vitamin $B_9$, *Rosa laevigata; Houttuynia cordata; Gardenia jasminoides; Polygoni multiflora; Lycium barbarum*; Ginsenoside re; and *Ixeris dentata*.

The constituents of the capsule-in-capsule liver supplement 400 include multiple inputs into the methionine cycle 100, which synergistically aid the body's use of the methionine cycle 100.

Outer Capsule

Still referring to FIG. 4, the outer capsule 410 is designed to dissolve in an acidic environment of the stomach, aided by gastric motion and/or enzymes, while the second set of constituents 422 of the inner capsule 420 are shielded/protected.

Choline

The first set of constituents 412, in the outer capsule 410, optionally and preferably contains choline 166. One requirement/burden placed of the human liver is to make choline. Choline is a water soluble essential nutrient. More particularly, choline comprises quaternary ammonium salts containing the trimethylethanolammonium cation and a counter anion, which is stable in stomach acids. The trimethylethanolammonium cation is optionally present in the head group of a phosphatidylcholine, a phospholipid, which is a major component of biological membranes, such as a cell wall, and aids in transport into/through cell membranes through forces related to hydrophilic/hydrophobic areas of the molecule. Thus, the first set of constituents 412, in the outer capsule 410, optionally and preferably contains phosphatidylcholine, which by containing choline, facilitates subsequent transport, such as through a wall of the small intestine, in blood, or into/through a cell wall.

Recent studies have shown that choline deficiency may have adverse effects. While it is not medically certain whether supplemental choline is beneficial to humans, the inventor notes that site-specific delivery of choline along with other constituents of the methionine cycle has not been addressed. Yet, possible benefits include reducing the risk of fatty liver disease. Hence, choline 166, an input to the methionine cycle 100, is co-introduced into the body with other elements of the capsule-in-capsule liver supplement 400 to facilitate the methionine cycle 100, allowing the body to regulate/drive related systems, such as liver function.

Like S-adenosyl methionine 140, choline 166 is a methyl donor, which has benefits described below. However, due to the selectivity of some reactions, such as steric and/or localized charge, in some instances choline 166 donates methyl groups where S-adenosyl methionine 140 does not and vise-versa. Hence, choline 166 and S-adenosyl methionine 140 are synergistic constituents of the capsule-in-capsule liver supplement 400.

To aid biotransport, timing of delivery, and to reduce stress on the body, the outer capsule 410 optionally and preferably contains the first set of constituents 412 in a phosphatidylcholine suspension.

The term phosphatidylcholine is sometimes used interchangeably with lecithin; however, choline is a component of phosphatidylcholine, which is a component of lecithin.

Inner Capsule

Still referring to FIG. 4, the inner capsule 420 of the capsule-in-capsule liver supplement 400 is designed to dissolve in the small intestine after partial or total protection in the acidic environment of the stomach. More particularly, the inner capsule 420 is enteric coated, which prevents dissolution in the gastric environment. Still more particularly, the enteric coating is stable at a stomach pH, such as about a pH of 3±1, and breaks down at a higher pH present in the small intestine, such as a pH of 7-9 or greater than a pH of 6. Thus, the second set of constituents 422 of the inner capsule 420 are shielded/protected from the low pH stomach environment and released in the small intestine in a formulated bioactive form ready for uptake through the walls of the small intestine into the bloodstream.

Methionine

The second set of constituents 422, in the inner capsule 420, optionally and preferably contains methionine 110. Methionine 110 is sulfur-containing amino acid, typically ingested in the form of dietary proteins. Here, the dietary protein is supplemented with methionine 110. Methionine 110 is used in the methionine cycle 100 to form homocysteine 120 and eventually cysteine 130 after activation with ATP 162 to form S-adenosyl methionine 140. More particularly, the methyl group of methionine is activated by the addition of adenosine to the sulfur of methionine, adjacent the methyl group, via use of energy from the adenosine triphosphate.

S-Adenosyl Methionine

The second set of constituents 422, in the inner capsule 420, optionally and preferably contains S-adenosyl methionine 110. S-adenosyl methionine 140 is the amino acid methionine 100 bound to a molecule of ATP 162. S-adenosyl methionine 140 circulates in the blood naturally and acts as a methyl donor to the methyl acceptor 142. Donating a methyl group to other molecules can accelerate or preserve reactions in the body as a form of metabolic maintenance. Thus, the body benefits from an adequate supply of S-adenosyl methionine 140 in the bloodstream. S-adenosyl methionine 140 aids in restoration of liver function in the presence of chronic liver diseases such as alcoholic and non-alcoholic cirrhosis as well as cholestasis. S-adenosyl methionine 140 functions as a methyl donor in the synthesis and formation of phosphatidylcholine and L-cysteine, which are both necessary for maintaining liver health.

Further, providing S-adenosyl methionine 140 in the capsule-in-capsule liver supplement 400 further aids the body as S-adenosyl methionine 140 is used to synthesize phosphatidyl choline.

Commonly used terms for S-adenosyl methionine 140 comprise:

S-adenosyl-L-methionine;
adenosylmethionine;
S-adenosylmethionine;
ademetionine;
S-adenosylmethionine butanedisulfonate;
S-adenosylmethionine tosylate;
S-adenosylmethionine tosylate disulfate;
AdoMet;
Ado Met;
SAM;
SAM-e;
SAMe; and
Sammy.

For clarity of presentation and without loss of generalization, S-adenosyl methionine 140 is also referred to herein as S-Adenosyl-L-methionine and/or SAMe.

Subsequent to activation of methionine 110 to form S-adenosyl methionine 140, S-adenosyl methionine 140 is primed for removal of the methyl group to form S-Adenosyl Homocysteine (SAH) 150, which is subsequently converted to homocysteine 120 through removal of the adenosine molecule. Homocysteine 120, in liver cells, enters the transsulfuration pathway, catalyzed by vitamin $B_6$, to produce cysteine 130. Thus, by providing S-adenosyl methionine 140 in the small intestine, optionally with other drivers of the methionine cycle 100, the body's ability to regulate the transsulfuration pathway in the liver is enhanced. The body optionally uses the homocysteine 120 to reform methionine 110.

Glycyrrhetinic Acid

The second set of constituents 422, in the inner capsule 420, optionally and preferably contains glycyrrhetinic acid or glycyrrhetic acid. Glycyrrhetinic acid is a pentacyclic triterpenoid derivative of the beta-amyrin type. Glycyrrhetinic acid is isolated from licorice plants, such as through hydrolysis of glycyrrhizic acid present in licorice. Glycyrrhetinic acid stimulates pancreatic secretion and mucous secretion in the intestines and markedly increase intestinal motility. Optionally, the capsule-in-capsule liver supplement 400 includes glycyrrhizin in the outer capsule 410 and/or in the inner capsule 420 in place of and/or in conjunction with glycyrrhetinic acid as glycyrrhetinic acid is the major metabolite of glycyrrhizin. However, delivery of bioactive glycyrrhetinic acid is preferred due to the synergistic benefit of simultaneous delivery of the capsule-in-capsule liver supplement 400 constituents, further described infra.

Silymarin

The second set of constituents 422, in the inner capsule 420, optionally and preferably contains silymarin or milk thistle. Milk thistle or silymarin is used in a natural treatment for liver disorders, such as cirrhosis, jaundice, and hepatitis. More particularly, silymarin inhibits fibrogenesis in the liver and has an antioxidant activity used to counter chronic liver diseases caused by oxidative stress, such as alcoholic and/or non-alcoholic fatty liver diseases and drug and/or chemical-induced hepatic toxicity.

Phosphatidylcholine

The second set of constituents 422, in the inner capsule 420, optionally and preferably contains phosphatidylcholine (PPC). As described, supra, phosphatidylcholine is a phospholipid that aids in transport into/through cell membranes through forces related to hydrophilic/hydrophobic areas of the phosphatidylcholine molecule. Thus, the second set of constituents 422, in the inner capsule 420, optionally and preferably contains phosphatidylcholine, which facilitates subsequent transport of members of the second set of constituents through a wall of the small intestine, in blood, and/or into/through a cell wall.

The inner capsule 420 optionally and preferably contains the second set of constituents 422 in a phosphatidylcholine suspension.

Additional Capsule-in-Capsule Constituents

Either capsule of the capsule-in-capsule liver supplement 400 optionally and preferably contains any natural product or supplement identified as beneficial to the methionine cycle 100, liver regulation, and/or for liver treatment, such as serine, to aid export of methionine cycle; trimethylglycine or betaine; vitamin $B_{12}$ 168; vitamin $B_6$; folate, such as folic acid and vitamin $B_9$; *Rosa laevigata*; *Houttuynia cordata*; *Gardenia jasminoides*; *Polygoni multiflora*; *Lycium barbarum*; Ginsenoside re; and/or *Ixeris dentata*, which are further described infra.

*Rosa laevigata*

Fruit of *Rosa laevigata*, an evergreen climbing shrub native to southern China and/or an extract thereof is optionally included in the capsule-in-capsule liver supplement 400, functioning as a sterol regulatory element-binding proteins inhibitor, at a mass of at least 0.1, 1, or 5 mg and less than 500 mg.

*Houttuynia cordata* is one a species in the genus *Houttuynia*, which is a flowering plant native to Southeast Asia. Optionally, *Houttuynia cordata* and/or an extract of *Houttuynia cordata*, at a mass of at least 0.1, 1, or 5 mg and less than 100, 500, 1000, or 2000 mg, is optionally included in the capsule-in-capsule liver supplement 400 functioning as a triglyceride and/or cholesterol reducing element in the liver.

*Gardenia jasminoides*

Fruit of *Gardenia jasminoides*, an evergreen flowering plant of the family Rubiaceae from Southeast Asia and/or an extract of *Gardenia jasminoides*, at a mass of at least 0.1, 1, or 5 mg and less than 1000 mg, is optionally included in the capsule-in-capsule liver supplement 400 functioning as fatty acid synthase inhibitor.

*Polygoni multiflora*

The radix, root, of *Polygoni multiflora*, a lipid regulator, is optionally included in the capsule-in-capsule liver supplement 400 with a mass of 1 to 300 mg.

*Lycium barbarum* L.

*Lycium barbarum* is a species of boxthorn in the family Solanaceae from which the goji berry or wolfberry is harvested, where *Lycium barbarum* decreases hepatic lipid accumulation. Optionally, *Lycium barbarum* L. and/or an extract, such as a water and/or ethanol extract, of *Lycium barbarum* L., at a mass of at least 0.1, 1, or 5 mg and less than 100, 500, 1000, or 2000 mg, is optionally included in the capsule-in-capsule liver supplement 400.

Ginsenoside Re

Ginsenoside-Re from *Panax ginseng* or Korean *ginseng* root is optionally included in the capsule-in-capsule liver supplement 400, functioning as a glycerol 3-phosphate acyltransferases inhibitor, at a concentration of at least 0.1, 1, or 5 mg and less than 250 mg.

*Ixeris dentata*

*Ixeris dentata* is in the dandelion family and is an Asian flowering plant. Optionally, *Ixeris dentata* and/or an extract of *Ixeris dentatal*, at a mass of at least 0.1, 1, or 5 mg and/or less than 50, 100, 250, or 500 mg, is optionally included in the capsule-in-capsule liver supplement 400 functioning as decreasing hepatic accumulation of lipids.

For clarity of presentation and without loss of generality, two examples of the capsule-in-capsule liver supplement 400 are provided.

Example I

In a first example, the capsule-in-capsule liver supplement 400 comprises two capsules, the outer capsule 410 and the inner capsule 420. The outer capsule 410 encases choline, preferably in a phosphatidylcholine suspension, where the outer capsule dissolves in a pH range of the stomach. The inner capsule 420 is encased in the outer capsule 410. The inner capsule 420 comprises an enteric coating, which dissolves in a pH range higher, more basic, than a stomach pH. For instance, the enteric coating is stable at a stomach pH of 3 and dissolves at a small intestine pH of 7, which results in release of the components of the inner capsule 420 in the small intestine. The inner capsule 410 encapsulates methionine, S-adenosyl methionine, glycyrrhetinic acid, and/or silymarin. Optionally and preferably, each of the water soluble methionine, S-adenosyl methionine, glycyrrhetinic acid, and/or silymarin are blended with phosphatidylcholine into a liposomal and/or emulsified form. Thus, the second set of constituents 422 of the inner capsule maintain a bioactive form after passage through the stomach cavity and dissolution in the small intestine and are already emulsified when delivered into the small intestine. Optionally, the outer capsule 410 and/or the inner capsule 420 additionally contain a liver aiding natural product.

Example II

In a second example, the capsule-in-capsule liver supplement 400 comprises one or more of choline, S-adenosyl methionine, glycyrrhetinic acid, silymarin, phosphatidylcholine, serine, trimethylglycine, betaine, vitamin $B_{12}$, vitamin $B_6$, folate, folic acid, and vitamin $B_9$ in a range of 0.1 to 2000 mg per individual component and more preferably in a range of 25 or 50 to 100, 250, 500, or 1000 mg per component. In one case, the capsule-in-capsule liver supplement 400 comprises 50 to 2000 mg of choline; 50 to 1000 mg of S-adenosyl methionine 140; 50 to 1000 mg of glycyrrhetinic acid; 10 to 500 mg of silymarin; and/or 50 to 3000 mg of phosphatidylcholine. In a second case, the capsule-in-capsule liver supplement 400 comprises 500±100 mg of choline 166, 500±100 mg of S-adenosyl methionine 140, 500±100 mg of glycyrrhetinic acid, 250±50 mg of silymarin, and/or 900±300 mg of phosphatidylcholine. In a third case, the capsule-in-capsule liver supplement 400 comprises 500±100 mg of choline 166 in the outer capsule 410 and 500±100 mg of S-adenosyl methionine 140, 500±100 mg of glycyrrhetinic acid and 250±50 mg of silymarin in the inner capsule 420, where either capsule contains up to 1000 mg of phosphatidylcholine. In a fourth case, in addition to any of choline 166, S-adenosyl methionine 140, glycyrrhetinic acid, silymarin, and/or phosphatidylcholine, the outer capsule 410 and/or the inner capsule 420 contains at least 0.1, 1, 5, 10, 25, or 50 mg of any one or more of: serine, trimethylglycine, betaine, vitamin $B_{12}$, vitamin $B_6$, folate, folic acid, vitamin $B_9$, *Rosa laevigata*, *Houttuynia cordata*, *Gardenia jasminoides*, *Polygoni multiflora*, *Lycium barbarum*, Ginsenoside re, and *Ixeris dentata*. In any case, the total weight of components of the capsule-in-capsule liver supplement 400 are contained in 1, 2, 3, 4, or 5 capsules, with the mass of each constituent distributed in any manner between the multiple capsules, such as evenly into three separate capsule in the capsule-in-capsule liver supplement 400.

Generally, the inventor has determined, in stark contrast to oral delivery of a liquid, delayed and simultaneous delivery into the small intestine, in a bioactive form, in a phosphatidylcholine suspension, liposome, and/or in an emulsified system, of one or more of choline 166, S-adenosyl methionine 140, glycyrrhetinic acid, silymarin, phosphatidylcholine, serine, trimethylglycine, betaine, vitamin $B_{12}$, vitamin $B_6$, folate, folic acid, vitamin $B_9$, *Rosa laevigata*, *Houttuynia cordata*, *Gardenia jasminoides*, *Polygoni multiflora*, *Lycium barbarum*, Ginsenoside re, and *Ixeris dentata* facilitates body regulation of the liver and related metabolic pathways due to the synergistic availability of multiple molecules used in the methionine cycle, liver, and/or liver regulation processes.

Embodiments are described partly in terms of functional components and various assembly and/or operating steps. Such functional components are optionally realized by any number of components configured to perform the specified functions and to achieve the various results. The systems and components described herein merely exemplify applications. Further, embodiments described herein, for clarity and without loss of generality, optionally use any number of conventional techniques for manufacturing, assembling, connecting, and/or operation. Components, systems, and apparatus described herein are optionally used in any combination and/or permutation.

In still yet another embodiment, the invention comprises and combination and/or permutation of any of the elements described herein.

Herein, any number, such as 1, 2, 3, 4, 5, is optionally more than the number, 0.5, 1, 2, 5, or 10 more than the number; less than the number; 0.5, 1, 2, 5, or 10 less than the number; and/or within 1, 2, 5, 10, 20, 50, or 100 percent of the number.

The particular implementations shown and described are illustrative of the invention and its best mode and are not intended to otherwise limit the scope of the present invention in any way. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for aiding regulation of a liver of a human body, comprising the steps of:
   providing for ingestion a dietary capsule-in-capsule liver supplement, comprising:
      an outer capsule comprising:
         an outer casing chemically configured to dissolve at a pH<4.0 during use in the stomach; and
         a first set of constituents emulsified in a first portion of phosphatidylcholine and contained within said outer casing, said first set of constituents comprising:
            at least 100 mg of choline, said choline comprising a quaternary ammonium salt of a trimethylethanolammonium cation and a counter anion stable at the pH<4 in the stomach;
      an inner capsule, fully encapsulated by said outer capsule, comprising:
         an outer enteric coating stable at the pH<4 in the stomach and configured to dissolve at a pH>6 in the small intestine; and
         a second set of constituents emulsified in a second portion of phosphatidylcholine and contained within said enteric coating, said second set of constituents comprising:
            at least 100 mg of S-adenosylmethionine;
            at least 100 mg of glycyrrhetinic acid; and
            at least 50 mg of silymarin;
   ingesting said capsule-in-capsule liver supplement;
   releasing in the stomach, through acidic dissolution of said outer casing, a form of said choline stable at the pH<4 in the stomach; and
   simultaneously co-releasing, through dissolution of said outer enteric coating at the pH>6, in the small intestine multiple pre-emulsified constituents used by the body in self-regulation of the liver, all of said multiple pre-emulsified constituents comprising a bioactive form of: the S-adenosylmethionine, the glycyrrhetinic acid, and the silymarin.

2. The method of claim 1, further comprising the step of: delivering, for uptake through a wall of the small intestine, the multiple pre-emulsified constituents for use by the body in protection against hepatotoxic agents.

3. The method of claim 2, further comprising the step of: encapsulating into said inner capsule of said capsule-in-capsule liver supplement at least three molecules, of differing molecular formula, directly used in a human methionine cycle.

4. The method of claim 3, further comprising the step of: incorporating into said inner capsule of said capsule-in-capsule liver supplement all of:
   a fatty acid synthase inhibitor;
   a natural sterol regulatory element-binding proteins inhibitor;
   a fatty acid synthase inhibitor; and
   a glycerol 3-phosphate acyltransferase inhibitor.

5. The method of claim 3, further comprising the step of: incorporating into said capsule-in-capsule liver supplement a natural sterol regulatory element-binding proteins inhibitor.

6. The method of claim 5, further comprising the step of: providing a liver cholesterol reducing natural product in said capsule-in-capsule liver supplement.

7. The method of claim 6, further comprising the step of: incorporating into said inner capsule of said capsule-in-capsule liver supplement a fatty acid synthase inhibitor.

8. The method of claim 7, further comprising the step of: incorporating into said inner capsule of said capsule-in-capsule liver supplement a glycerol 3-phosphate acyltransferases inhibitor.

9. The method of claim 8, further comprising the step of: incorporating into said inner capsule of said capsule-in-capsule liver supplement at least 1.0 mg of *Ixeris dentata*.

10. A dietary supplement for uptake, after passing through a stomach, through a wall of a small intestine of a human, comprising:
   a capsule-in-capsule liver supplement, comprising:
      an outer capsule comprising:
         an outer casing chemically configured to dissolve at a pH<4.0 during use in the stomach; and a first set of constituents emulsified in a first portion of phosphatidylcholine and contained within said outer casing, said first set of constituents comprising:
  at least 100 mg of choline, said choline comprising a quaternary ammonium salt of a trimethylethanolammonium cation and a counter anion stable at the pH<4 in the stomach;
an inner capsule, fully encapsulated by said outer capsule, comprising:
  an outer enteric coating stable at the pH<4 in the stomach and configured to dissolve at a pH>6 in the small intestine; and
  a second set of constituents emulsified in a second portion of phosphatidylcholine and contained within said enteric coating, said second set of constituents comprising:
    at least 100 mg of S-adenosylmethionine;
    at least 100 mg of glycyrrhetinic acid; and
    at least 50 mg of silymarin.

11. The supplement of claim 10, said inner capsule further comprising:
at least three chemically distinct molecular components directly used in a human methionine cycle.

12. The supplement of claim 11, said inner capsule further comprising all of:
a liver triglyceride reducing natural product;
a fatty acid synthase inhibitor; and
a glycerol 3-phosphate acyltransferases inhibitor.

13. The supplement of claim 12, said inner capsule further comprising:
a sterol regulatory element-binding protein inhibitor.

14. The supplement of claim 13, said inner capsule further comprising a small chain alcohol extraction of goji berry, said small chain alcohol comprising less than seven carbon atoms per molecule.

15. The supplement of claim 14, further comprising:
a set of natural products encapsulated in said capsule-in-capsule liver supplement, comprising at least three of:
  at least 1.0 mg of *Rosa laevigata;*
  at least 1.0 mg of *Houttuynia cordata;*
  at least 1.0 mg of *Gardenia jasminoides;*
  at least 1.0 mg of *Polygoni multiflora;* and
  at least 1.0 mg of *Lycium barbarum.*

16. The supplement of claim 14, further comprising:
a set of natural products encapsulated in said capsule-in-capsule liver supplement, comprising all of:
  at least 1.0 mg of the *Rosa laevigata;*
  at least 1.0 mg of the *Houttuynia cordata;*
  at least 1.0 mg of the *Gardenia jasminoides;*
  at least 1.0 mg of the *Polygoni multiflora;* and
  at least 1.0 mg of the *Lycium barbarum.*

* * * * *